Figure 1:
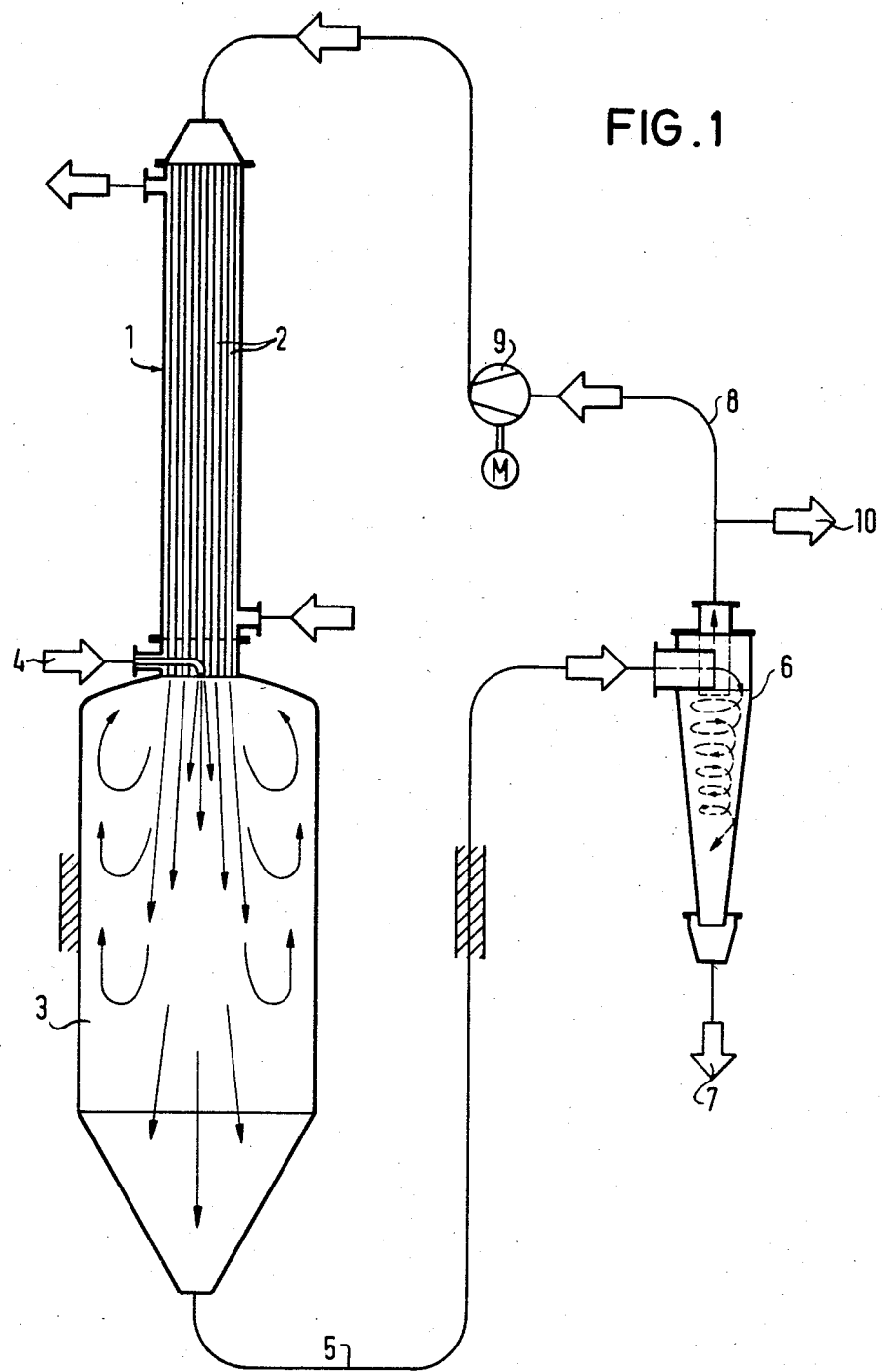

United States Patent [19]

Klima et al.

[11] Patent Number: 4,591,493
[45] Date of Patent: May 27, 1986

[54] PROCESS FOR OBTAINING SOLID CYANURIC CHLORIDE

[75] Inventors: Hubertus Klima, Tacherting; Herbert Jekat, Schopfheim, both of Fed. Rep. of Germany

[73] Assignee: SKW Trostberg Aktiengesellschaft, Trostberg, Fed. Rep. of Germany

[21] Appl. No.: 714,957

[22] Filed: Mar. 22, 1985

[30] Foreign Application Priority Data

Apr. 13, 1984 [DE] Fed. Rep. of Germany ....... 3414097

[51] Int. Cl.⁴ ........................................... C01B 21/088
[52] U.S. Cl. .................................... 423/383; 423/364; 423/371
[58] Field of Search ......................... 423/371, 364, 383

[56] References Cited

U.S. PATENT DOCUMENTS 3,141,882  7/1964  Tilo ..................................... 260/248

FOREIGN PATENT DOCUMENTS 948271  1/1964  United Kingdom .

Primary Examiner—Curtis R. Davis
Attorney, Agent, or Firm—Felfe & Lynch

[57] ABSTRACT

The present invention provides a process for obtaining solid cyanuric chloride from a cyanuric chloride vapor obtained by the trimerization of cyanogen chloride, wherein the cyanuric chloride vapor is introduced into the upper part of a separation chamber in the center of many individual cold inert gas streams, the solid cyanuric chloride, after emergence thereof from the separation chamber, is separated from the inert gas stream by the action of centrifugal and gravitational force and the inert gas, together with a residual content of very finely crystalline cyanuric chloride, is returned, after cooling thereof, as part streams to the separation chamber.

11 Claims, 2 Drawing Figures

PROCESS FOR OBTAINING SOLID CYANURIC CHLORIDE

The present invention is concerned with a process for obtaining solid cyanuric chloride from cyanuric chloride vapour obtained by the trimerisation of cyanogen chloride.

As a technical intermediate product, cyanuric chloride is of considerable technical importance for the production of dyestuffs, plant protection agents and pharmaceuticals, as well as of textile and rubber adjuvants and is obtained, after the catalytic trimerisation of cyanogen chloride, in gaseous form, together with unreacted cyanogen chloride and chlorine. This gas mixture is usually passed into separation chambers, the cyanuric chloride being deposited on the cooled walls thereof. A disadvantage of this manner of desublimation is that the cyanuric chloride deposits on the walls and the removal devices in the form of coarse crystals and thus negatively influences the heat transition. The regular knocking off of cakings from the walls merely results in a brief improvement of the heat transfer. Furthermore, because of the increasing damage to the separator and the noise nuisance, this method is in no way satisfactory, quite apart from the poor quality of the product obtained in this manner.

According to Federal Republic of Germany Patent Specification No. 12 66 308, an attempt has been made to solve this problem by spraying the cyanuric chloride, together with a readily volatile cooling liquid, for example methylene chloride or chloroform. In this way, there is admittedly obtained a finely-divided cyanuric chloride but the recovery of the cooling liquid is technically very laborious. In addition, blockages of the spray nozzles used can very easily occur.

Instead of the direct deposition of the cyanuric chloride vapour, it has been suggested, for example, in Federal Republic of Germany Patent Specification Nos. 25 37 673 and 23 32 636 to liquify the cyanuric chloride present in the reaction gas before the solidification and subsequently to spray, the removal of the heat of desublimation giving rise to smaller problems and the chlorine and cyanogen chloride can be removed before the solidification. However, this two-stage deposition process is technically laborious.

This disadvantage is also displayed by the processes according to Federal Republic of Germany Patent Specification Nos. 28 43 381 and 28 43 382 for obtaining solid or liquid cyanuric chloride in which the reaction mixture obtained after trimerisation of cyanogen chloride is passed into an apparatus combination consisting of a distilling off column and condenser and, by temperature regulation at the outlet of the condenser, the cyanuric chloride is partly condensed in the column, whereas the gaseous portion, which emerges from the head of the column, is desublimated in conventional deposition chambers. However, this process gives rise to high operational and investment costs.

Therefore, it is an object of the present invention to provide a process for obtaining solid cyanuric chloride which does not display these disadvantages of the prior art and which, without great technical expense, makes it possible to produce a finely particulate cyanuric chloride with a narrow grain spectrum.

Thus, according to the present invention, there is provided a process for obtaining solid cyanuric chloride from the cyanuric chloride vapour obtained by the trimerisation of cyanogen chloride, wherein the cyanuric chloride vapour is introduced into the upper part of a separation chamber in the centre of many individual cold inert gas streams, the solid cyanuric chloride, after emergence thereof from the separation chamber, is separated off from the inert gas stream by the action of centrifugal and gravitational force and the inert gas, together with the residual content of very finely crystalline cyanuric chloride, is returned, after cooling thereof, as part streams to the separation chamber.

Surprisingly, we have found that, with the process according to the present invention, there can be obtained a very finely divided cyanuric chloride of very high purity. Furthermore, a rapid deposition of the solid cyanuric chloride is possible without problems arising in the removal of heat due to cakings on the wall or stoppages.

According to the present invention, the reaction mixture obtained in the production of the cyanuric chloride is passed into the upper part of the separation chamber in such a manner that it is present in the centre of many individual cold streams of inert gas and is thus enveloped by the inert gas. In this way, contact of the cyanuric chloride vapour with the walls of the separator is prevented and the formation of coarse crystals or agglomerates is also prevented.

The streams of inert gas preferably have a temperature of from 0° to 40° C., the range of from 15° to 30° C. being especially preferred. In this temperature range, the chilling effect by the inert gas is sufficient in every case. The inert gas preferably enters the separation chamber with a velocity of from 40 to 80 meters per second, a good mixing with the cyanuric chloride vapour and a rapid separation of the solid material thereby being achieved.

The division of the inert gas stream into individual partial streams takes place by means of cooling tubes which are arranged concentrically to the cyanuric chloride inlet pipe. The amount of inert gas preferably amounts to 50 to 100 times the amount of cyanuric chloride.

As inert gas, there can, in principle, be used all gases which do not enter into reaction with the cyanuric chloride vapour at the prevailing temperatures. For economic reasons, dry air or nitrogen are especially preferred.

After the separation of the cyanuric chloride, the finely-divided solid material particles leave the separation device, together with the warmed up inert gas, and are subjected to the action of centrifugal and gravitational force, a partial separation of the gas from the solid material thereby taking place. This separation preferably takes place in a cyclone. The inert gas then still has a residual content of very finely divided crystalline cyanuric chloride. This residual content of very finely divided cyanuric chloride particles is important since these particles, together with the inert gas, after compression thereof and cooling in a heat exchanger, are again passed to the separation chamber and there act as crystallisation nuclei. In this way, the desublimation of the vaporous cyanuric chloride becomes a controlled crystallisation procedure. The entrained very fine particles influence the velocity of the desublimation and thus the particle size of the deposited cyanuric chloride.

It is especially advantageous to limit the circulating very fine particles of cyanuric chloride to a particle size of less than 5 $\mu$m. For this purpose, the centrifugal and gravitational force is allowed to act in such a manner that all particles which are larger than 5 μm. are separated out as solid material particles and that the particles with a particle size of less than 5 μm. remain in the inert gas. It is thereby preferred that the amount of particles remaining in the inert gas amount to 15 to 20% by weight of the total amount of the cyanuric chloride.

Since the inert gas stream from which the solid material particles have been separated off still contains small amounts of contaminations of cyanogen chloride or chlorine, it is necessary continuously to withdraw a part of the inert gas before its compression and cooling and to purify this by conventional processes.

In a preferred embodiment of the process according to the present invention, on the head of the separation chamber there is incorporated a central pipe which consists of a mixing pipe and a diffuser. The inert, cold gas emerging from the cooler is passed into this central pipe. It acts as a driving stream and sucks in a large amount of circulating gas of higher temperature from the outer annular gap of the separation chamber. After mixing of the two gas streams, there is obtained a temperature which is higher than that obtained without this device. The hot cyanuric chloride vapour is passed into this zone, the chilling effect thereby being moderate. Furthermore, by means of this device, very fine crystals are repeatedly passed through the zone of the supersaturated breakdown. From these two effects results a somewhat coarser granular product.

Also in the case of this variant of the process, there are obtained the advantages of the process according to the present invention, such as high capacity density, avoidance of cakings, rapid separation velocity and a narrow particle size spectrum.

Figure 2:
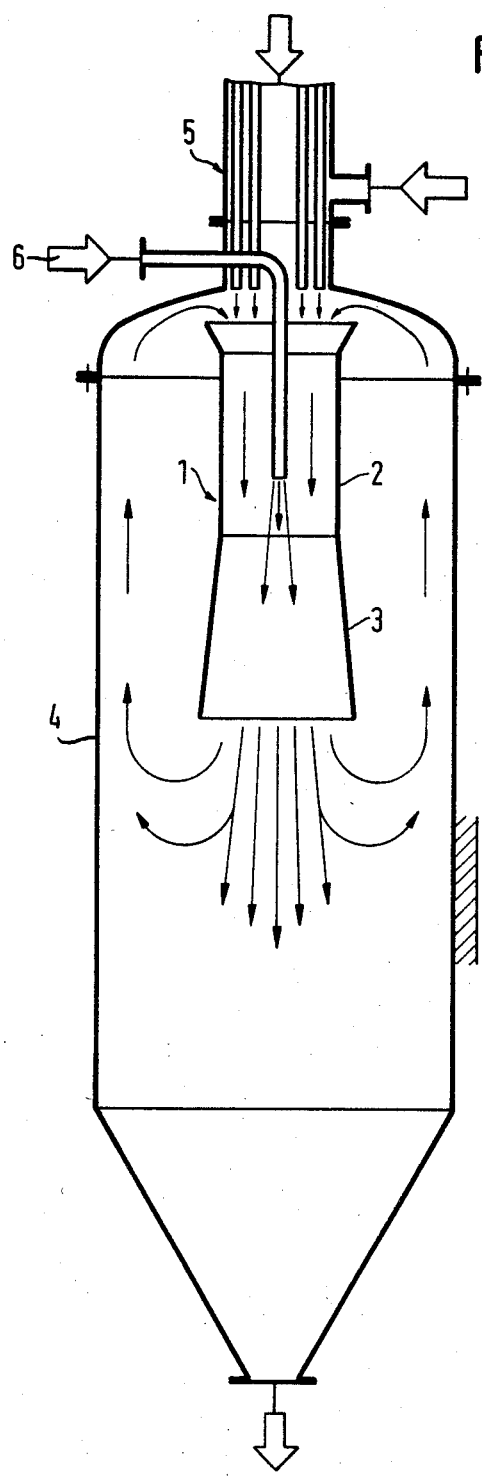

FIGS. 1 and 2 of the accompanying drawings show preferred embodiments of the process according to the present invention.

According to FIG. 1, inert gas, cooled in a cooler 1 to an appropriate temperature, enters into a separation chamber 3 with a high velocity through several individual pipes 2. Cyanuric chloride vapour is introduced via pipe 4 into the centre of the divided inert gas streams. After the separation, the inert gas and the solid material particles leave the separation chamber via a pipe 5 and are passed to a cyclone 6 in which a partial separation of the gas from the solid material takes place in such a manner that the main amount of the solid material is removed via pipe 7, whereas the inert gas with a residual content of very fine crystalline cyanuric chloride is again passed via pipe 8 and a compressor 9 to the cooler 1. For the purification of the inert gas, a partial stream can be branched off via pipe 10 to a gas wash.

In FIG. 2, there is shown a further preferred process variant. A central pipe 1, which consists of a mixing pipe 2 and a diffuser 3, is present on the head of the separation chamber 4. Cold inert gas emerges at a high velocity from a cooler 5 and is introduced into the mixing pipe 2. It sucks in warmer circulating gas from the annular space of the separation chamber 4. After mixing of both streams has taken place, the hot cyanuric chloride vapour 6 is introduced and chilled in the centre of the mixed gas. In the diffuser 3, there takes place a pressure increase which favours the circulation around the central pipe 1. The removal and the recycling of the inert gas takes place in the manner illustrated in FIG. 1.

The following Examples are given for the purpose of illustrating the present invention:

EXAMPLE 1

An experiment was carried out according to FIG. 1 in the case of which the cyanuric chloride was separated out under the following conditions:
mass stream of cyanuric chloride: 12 kg./h.
volume stream of inert gas: 1000 $m^3{}_N$/h.
residual content of crystalline cyanuric chloride in the inert gas after centrifugal separation: 450 mg./$m^3$
particle size of the residual cyanuric chloride in the inert gas (separation particle size of the cyclone): 5 μm.
temperature of the inert gas at the cooler outlet: 20° C.
velocity of the inert gas at the cooler outlet: 44 m/s.
temperature of the inert gas at the separator outlet: 26° C.

Results

The sieve analysis of the product obtained gave a particle size division of 98% smaller than 63 μm. The bulk density was 260 g./l. The purity of the cyanuric chloride obtained was 98.4 to 99.2%.

The usefulness of the cyanuric chloride obtained for the production of triazine herbicides could be demonstrated with very good effect.

EXAMPLE 2

In the case of an experiment according to FIG. 2, the following operating data were adjusted and the following results obtained:
mass stream of cyanuric chloride: 10.5 kg./h.
volume stream of inert gas: 850 $m^3{}_N$/h.
residual content of crystalline cyanuric chloride in the inert gas after the centrifugal separation: 510 mg./$m^3$
particle size of the residual cyanuric chloride in the inert gas (separation particle size of the cyclone): 5 μm.
temperature of the inert gas at the cooler outlet: 20° C.
temperature of the inert gas at the end of the mixing zone: 26.5° C.
temperature of the inert gas at the separator outlet: 27° C.

Results

The sieve analysis of this product gave the following particle size distribution:
>250 μm.: 1.06%
125–250 μm.: 4.91%
63–125 μm.: 15.56%
<63 μm.: 78.47%
The bulk density of the cyanuric chloride product was 914 g./l.

We claim:

1. A process for obtaining finely divided high purity solid cyanuric chloride from a cyanuric chloride vapour containing reaction mixture resulting from the catalytic trimerization of cyanogen chloride and including unreacted cyanogen chloride or chlorine or a mixture thereof, comprising the steps of:
   introducing a stream of the cyanuric chloride vapor containing reaction mixture into the upper part of a separation chamber in the center of a plurality of individual cold inert gas streams of gas which does not react with cyanuric chloride, said gas streams being cool relative to the cyanuric chloride vapor containing reaction mixture and mixing therewith within the chamber to crystalize the cyanuric chloride, removing the gas streams and cyanuric chloride from the separation chamber and separating the cyanuric chloride crystals from the inert gas stream from recovery, and cooling the inert gas, together with residual content of very finely crystalline cyanuric chloride for return to the separation chamber to comprise the inert gas streams.

2. The process of claim 1, wherein a central pipe is provided in the separation chamber, further comprising mixing the cold inert gas with warmer circulating gas from the separation chamber, in said pipe, whereafter the mixing with the cyanuric chloride vapour takes place.

3. The process of claim 1, wherein the cold inert gas streams are at a temperature of from about 0° to 40° C.

4. The process of claim 3, wherein the cold inert gas streams are at a temperature of from 15° to 30° C.

5. The process of claim 3 wherein the cold inert gas streams are introduced into the separation chamber with a velocity of from 40 to 80 meters per second.

6. The process of claim 3 wherein the cold inert gas streams are introduced in a 50 to 100 fold excess, referred to the amount of cyanuric chloride vapour.

7. The process of claim 3 wherein the separation action of centrifugal and gravitational force leaves the inert gas with a residual content of 15 to 20% by weight of very finely divided cyanuric chloride, referred to the total weight of the cyanuric chloride.

8. The process of claim 7 wherein the residual content of very fine cyanuric chloride has a particle size of which is less than 5 $\mu$m.

9. The process of claim 1 wherein the cold inert gas streams are introduced into the separation chamber with a velocity of 40 to 50 meters per second.

10. The process of claim 1 wherein the cold inert gas streams are introduced in a 50 to 100 fold excess referred to the amount of cyanuric chloride vapour.

11. The process of claim 1 wherein the solid cyanuric chloride is separated by use of centrifugal and gravitational forces.

* * * * *